United States Patent [19]

Greenberg et al.

[11] Patent Number: 4,940,577
[45] Date of Patent: Jul. 10, 1990

[54] ESTER BASED WATER-IN-OIL COSMETIC MICROEMULSIONS

[75] Inventors: Stephen M. Greenberg, New York; Louis A. Frischling, Lawrence, both of N.Y.

[73] Assignee: Lipo Chemicals Inc., Paterson, N.J.

[21] Appl. No.: 185,860

[22] Filed: Apr. 25, 1988

[51] Int. Cl.$^5$ .......................... A61K 7/42; A61K 7/44; A61K 9/107
[52] U.S. Cl. .......................... 424/59; 424/60; 514/941; 514/943
[58] Field of Search ................. 424/59; 514/941, 943

[56] References Cited

U.S. PATENT DOCUMENTS

| | | | |
|---|---|---|---|
| 3,651,102 | 3/1972 | Coopersmith | 514/873 |
| 4,370,319 | 1/1983 | Chapin et al. | 514/943 |
| 4,562,067 | 12/1985 | Hopp et al. | 424/59 |
| 4,603,046 | 7/1986 | Georgalas et al. | 424/59 |

FOREIGN PATENT DOCUMENTS

| | | | |
|---|---|---|---|
| 060372 | 9/1982 | European Pat. Off. | 514/941 |
| 0084341 | 7/1983 | European Pat. Off. | 514/943 |

*Primary Examiner*—Dale R. Ore
*Attorney, Agent, or Firm*—Anthony Lagani, Jr.

[57] ABSTRACT

A cosmetic composition comprising an ester containing emulsion, an emulsifier having the empirical formula

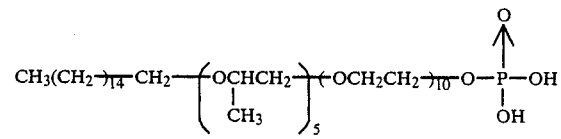

and a minor amount of water. The composition is a clear, water-in-ester microemulsion having the feel of mineral oil. Sunscreen additives and other active cosmetic ingredients can be incorporated into the blend.

18 Claims, No Drawings

ESTER BASED WATER-IN-OIL COSMETIC MICROEMULSIONS

FIELD OF THE INVENTION

This invention relates to water-in-ester microemulsions useful in cosmetics. In particular, it relates to microemulsions of esters utilizing an organic phosphate emulsifying agent.

BACKGROUND OF THE INVENTION

Water-in-oil emulsions are well known in the cosmetic art. While it is possible to prepare clear water-in-oil emulsions, these are generally "ringing gel" type microemulsions containing high levels of surfactants, e.g. 40–50%. They cannot be thinned down to flowable lotions without becoming opaque. Furthermore, these gels are generally heavy, sticky, tacky gels, and therefore, are cosmetically undesirable. The emulsifiers used to prepare them are polyhydric alcohols, ethoxylated alcohols, lanolin alcohols, ethoxylated lanolins, etc. There is a preference among users of skin care products for clear tanning oils which posses a smooth, non-tacky feel upon application.

Sunscreens are well known in the cosmetic art as useful to prevent sun burn and sun exposure related irritation. Sunscreen lotions are rated according to there effectiveness using a Sun Protection Factor (SPF) on a scale of 0 to 15; 0 representing no protection and 15 representing total sun block. However, there are products marketed which have SPF values greater than 15.

In general, sunscreen products are oil in water emulsions containing about 50 to 75% water. It has not been possible, heretofore, to produce tanning oil products with a SPF of greater than six without the use of large quantities of water or other polar materials. It is believed that this is because the known sunscreen agents require the presence of a polar compound such as alcohol or water to make &hem more effective (increase SPF).

In the past, it has been necessary to use high concentrations of sunscreen agents to produce clear tanning oils with an SPF value of 6. There is an available market for such clear tanning oils, since most users of sunscreens prefer tanning oils to the conventional water based emulsions which are usually opaque white or yellowish in color. These oil-in-water emulsions of the prior art contain about 50 to 75 weight percent water; minor amounts of esters are added to improve their feel.

There is a ready market for a water-in-oil type emulsifier for emollient and other cosmetic uses, which has a dry, oily feel and spreads on with a smooth, non-tacky feel. In particular, what is needed to satisfy the demand of those who find the use of the conventional oil-in-water sunscreen emulsions objectionable, is a tanning oil containing only sufficient amounts of water to make the sunscreen agents effective, while at the same time being clear microemulsion systems with an elegant oily feel.

SUMMARY OF THE INVENTION

It has surprisingly been found that clear water-in-ester micro emulsions having relatively low water content, useful as emollients and other cosmetic products, can be prepared utilizing esters as the oil phase and PPG-5-ceteth-10 phosphate as the sole emulsifier. The preferred esters are neopentyl glycol dicaprylate/dicaprate, tridecyl stearate, tridecyl trimellitate.

In particular, it has been found that an oily sunscreen having a high SPF can be prepared utilizing esters as the oil phase and PPG-5-ceteth-10 phosphate as the sole emulsifier. Not withstanding the fact that these sunscreens have an oily feel similar to anhydrous tanning oils, they have an SPF of 10 or greater.

The emulsifier is utilize at about 8 to 25 wt. %, with about 2 to about 15 wt. % water. The ester comprises about 20 to 90 wt. % of the composition.

DETAILED DESCRIPTION OF THE INVENTION

This invention relates to water-in-ester microemulsions useful as emollients, cosmetic creams and sun tan lotions. In particular, it relates to such compositions where the oil phase is an ester and the emulsifier is PPG-5-ceteth-10 phosphate, a phosphate ester having the empirical formula:

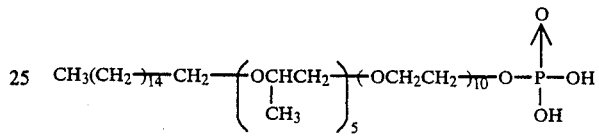

having the Lipo Chemical, Inc. designation, Lipophos TA.

The ester useful in the practice of this invention can be the reaction product of a $C_8$ to $C_{18}$ fatty acid and an alcohol which is a mono to hexahydryl, straight or branched chain alcohol. Illustrative non-limiting examples of such esters are tridecyl stearate, tridecyl trimellitate, neopentyl glycol dicaprylate/dicaprate, dipentaerythrityl hexacaprylate/hexacaprate and octyl palmitate.

It will be appreciated by those skilled in the art having access to this disclosure that mixtures of esters can be used. The ester blend can comprise about 1 to 99 wt. % of two or more esters.

Wherever "weight percent" or "wt. %" is used in the specification and claims to specify a quantity of a component it means weight percent based on the total emulsion.

The emulsion comprises about 2 to about 15 wt. % water, about 8 to about 25 wt. % emulsifier and about 20 to 90 wt. % ester. Preferably, the water is utilized at about 3 to 10 wt. %, e.g. 4 to 8 wt. percent. The preferred range of ester utilization is 30 to about 75 wt %; more preferably about 40 to about 60 wt. %. The emulsifier is utilized at about 8 to about 25 wt. % based on the total microemulsion; preferably about 10 to about 22 wt. %; more preferably about 12 to about 20 wt. %. Other active agents may be added depending on the desired end use of the product. The basic formula has application as water in-oil or water-in-ester microemulsions useful as cosmetically elegant lotions or tanning oils.

The aqueous phase can consist of only water and emulsifier. However, it can comprise various additional water soluble active ingredients such as propylene glycol, butylene glycol, Liponic EG-1 (Glycerth-26, Polyoxyethylene-26-glyceryl ether) Unipertan ® P-24 (a blend of hydrolyzed animal collagen, tyrosine and riboflavin), water soluble polyhydric alcohol ethoxylates, dihydroxyacetone (a simulated tan inducer) water soluble biological or botanical actives, etc. Other additives which can be utilized include fragrances, preservatives, volatile silicones and sunscreen agents.

As used in the specification and claims the term "sunscreen agent" means those compounds known to inhibit sun burn, sun poisoning, or other irritation resulting from over exposure to the sun. A substantial list of such compounds is described in the FDA Notice of Proposed Rule Making, published in the Federal Register, Friday, Aug. 25, 1978, Part II entitled "SunScreen Drug Product For Over The Counter Human Drugs; Proposed Saftey, Effect and Labeling Conditions" incorporated herein by reference. See also the Code of Federal Regulations, 21 C.F.R. Part 352. Illustrative, non-limiting examples of such sunscreens are benzophenone-3, octyl salicylate, octyl dimethyl PABA and octyl methoxycinnamate. Of course, active ingredients soluble in the ester may additionally be incorporated into the ester phase of the emulsion.

Where sunscreen agents are utilized they are preferably incorporated into the blend at about 8 to about 30 weight percent; preferably at about 10 to about 25 weight percent; more preferably 10 to 20 weight percent. It will be appreciated by those skilled in the art having access to this disclosure, that each sunscreen agent utilized has an upper safe limit fixed by the FDA, and the sunscreen agents utilized in the practice of this invention should be utilized within those limits. While a single sunscreen agent can be used it is preferred that a blend of at least two sunscreen agents be utilized to obtain an enhanced effect.

Where the volatile silicone is used it can be utilized at about 2 to about 15 wt. % of the overall composition. Ethyl alcohol can comprise about 1 to 15 wt. % of the overall composition. Preferably, the ethyl alcohol is used in conjunction with the volatile silicone at about 1 to 99 wt. % of the mixture; more preferably at about 30 to about 60% of the silicone/alcohol mixture. The silicone/alcohol blend is utilized at about 2-30 wt. % based on the microemulsion. The advantages of the instant invention may be more readily appreciated by reference to the following illustrative examples.

EXAMPLE I - EMOLLIENT LOTION

A. The following formulation was utilized to prepare an emollient lotion:

| Component | Weight Percent |
|---|---|
| Water | 6.0 |
| Lipophos TA | 24.0 |
| Liponate NPGC-2* | 70.0 |

*Neopentyl glycol dicaprylate/dicaprate

B. While this emollient formulation is within the scope of this invention, and is an adequate product, the smoothness of application can be enhanced by the addition of volatile silicone fluid and an alcohol. The following formulation illustrates an emollient utilizing volatile silicones:

| Component | Weight Percent |
|---|---|
| Water | 4.0 |
| Lipophos TA | 16.0 |
| Liponate NPGC-2 | 50.0 |
| Alcohol SD40B (200 proof) | 15.0 |
| Silicone 245 Fluid* | 15.0 |

*Cyclomethicone

EXAMPLE II - CLEAR TANNING WATER-IN-OIL MICROEMULSION HAVING AN SPF OF 10 PLUS

A clear tanning water-in-oil microemulsion having an SPF of 10 plus is prepared from the following formulation:

| Component | Weight Percent |
|---|---|
| Water | 4.0 |
| Lipophos TA | 16.0 |
| Liponate TDS+ | 54.0 |
| Octyl Dimethyl PABA | 7.5 |
| Octyl Methoxycinnamate | 7.5 |
| Benzophenone-3 | 6.0 |
| Octyl Salicylate | 5.0 |

+Tridecyl Stearate

The last four components of the formulation are sunscreen agents The formulation has an SPF of about 10+; a heretofore unattainable level for a composition having the smooth, oily feel of tanning oils. Not withstanding the fact that the product is a water-in-ester microemulsion, it is clear and has a dry, oily feel. Variations in feel can be achieved by using different esters or blends of esters. Similarly, silicone fluids can be utilized as in Example I, either alone or in combination with alcohol to modify the feel of the composition.

What is claimed is:

1. A clear, water-in-ester microemulsion composition comprising:
   (a) water at about 2 to 15% by weight of the emulsion;
   (b) as the sole emulsifier, a phosphate ester emulsifier having the empirical formula:

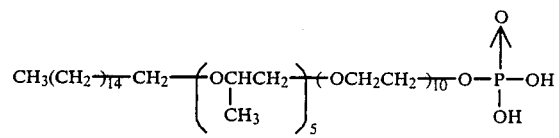

(c) at least one ester selected from the group consisting of neopentyl glycol dicaprylate/dicaprate, tridecyl stearate, tridecyl trimellitate, dipentaerythrityl hexacaprylate/hexacaprate, octyl palmitate and mixtures thereof.

2. The composition according to claim one wherein the ester component comprises a blend of at least two esters.

3. The composition according to claim 1 wherein the ester is selected from the group consisting of neopentyl glycol dicaprylate/dicaprate, tridecyl stearate, tridecyl trimellitate, dipentaerythrityl hexacaprylate/hexacaprate, octyl palmitate and mixtures thereof.

4. The composition according to claim 1 wherein the water is utilized at about 2 to 15 wt. %, the ester component is utilized at about 20 to 90 wt. %, and the emulsifier is utilized at about 8 to about 25 wt. %.

5. The composition according to claim 1 wherein the water is utilized at about 3 to about 10 weight %.

6. The composition according to claim 1 wherein the ester is utilized at about 30 to about 75 weight %.

7. The composition according to claim 1 wherein the emulsifier is utilized at about 10 to about 22 wt. %.

8. The composition according to claim 1 wherein the ester is utilized at about 40 to about 60 weight %.

9. The composition according to claim 1 wherein the emulsifier is utilized at about 12 to about 20 wt. %.

10. The composition according to claim 1 wherein the ester component is a blend of at least two esters selected from the group consisting of neopentyl glycol dicaprylate/dicaprate, tridecyl stearate, tridecyl trimellitate, dipentaerythrityl hexacaprylate/hexacaprate.

11. The composition according to claim 1 wherein the ester component is neopentyl glycol dicaprylate/-dicaprate.

12. The composition according to claim 1 wherein the water is utilized at about 3 to 10 wt. %, the ester component is utilized at about 40 to 60 wt. %, the emulsifier is utilized at about 12 to about 20 wt. %., and the ester is tridecyl stearate, or neopentyl glycol dicaprylate/dicaprate.

13. The composition according to claim 1 wherein at least one sunscreen agent is incorporated into the composition.

14. The composition according to claim 1 wherein at least one sunscreen agent is incorporated into the composition at about 8 to about 30 wt. %.

15. The composition according to claim 1 wherein at least one sunscreen agent is incorporated into the composition at about 10 to about 25 wt. %.

16. The composition according to claim 13 wherein the sunscreen agent is selected from the group consisting of Octyl Dimethyl PABA, Octyl Methoxycinnamate, Benzophenone-3, Octyl Salicylate and mixtures thereof.

17. The composition according to claim 16 wherein an effective amount of a blend of sunscreen agents is incorporated into the emulsion, said blend comprising Octyl Dimethyl PABA, Octyl Methoxycinnamate, Benzophenone-3 and Octyl Salicylate.

18. The composition according to claim 1 wherein a volatile silicone is added at about 2 to about 15 wt. % of the total emulsion.

* * * * *